United States Patent
Saji et al.

(10) Patent No.: US 8,476,449 B2
(45) Date of Patent: Jul. 2, 2013

(54) RADIOACTIVE IODINE LABELED ORGANIC COMPOUND OR SALT THEREOF

(75) Inventors: Hideo Saji, Kyoto (JP); Masahiro Ono, Kyoto (JP); Ikuya Seki, Tokyo (JP)

(73) Assignees: Nihon Medi-Physics Co., Ltd., Tokyo (JP); Kyoto University, Kyoto (JP)

( * ) Notice: Subject to any disclaimer, the term of this patent is extended or adjusted under 35 U.S.C. 154(b) by 0 days.

(21) Appl. No.: 13/582,047

(22) PCT Filed: Feb. 24, 2011

(86) PCT No.: PCT/JP2011/001075
§ 371 (c)(1),
(2), (4) Date: Aug. 30, 2012

(87) PCT Pub. No.: WO2011/108236
PCT Pub. Date: Sep. 9, 2011

(65) Prior Publication Data
US 2012/0330024 A1      Dec. 27, 2012

(30) Foreign Application Priority Data
Mar. 1, 2010  (JP) ................. 2010-061477

(51) Int. Cl.
| C07D 405/06 | (2006.01) |
| C07D 405/14 | (2006.01) |
| C07D 417/06 | (2006.01) |
| C07D 417/14 | (2006.01) |
| C07F 7/22   | (2006.01) |

(52) U.S. Cl.
USPC ...... 548/103; 548/183; 548/313.1; 548/316.1

(58) Field of Classification Search
None
See application file for complete search history.

(56) References Cited

U.S. PATENT DOCUMENTS
7,947,717 B2 * 5/2011 Pellecchia ............... 514/369

FOREIGN PATENT DOCUMENTS
| JP | 2004-067659 | 4/2004 |
| WO | WO 02/085903 A2 | 10/2002 |
| WO | WO 2004/054978 A1 | 7/2004 |
| WO | WO 2007/135890 A1 | 11/2007 |
| WO | WO 2009/054497 A1 | 4/2009 |

OTHER PUBLICATIONS

Brunden et al., "Advances in tau-focused drug discovery for Alzheimer's disease and related taupathies", Nature Reviews, Oct. 2009, vol. 8, 783-793.
Bulic et al., "Rhodanine-Based Tau Aggregation Inhibitors in Cell Models of Tauopathy", Angewandte Chemie International Edition, 2007, 46, 9215-9219.
English translation of International Application No. PCT/JP2011/001075, International Preliminary Report on Patentability under Chapter I, dated Sep. 4, 2012, 4 pages.
English translation of JP application No. 2012-503002, Notice of Reasons for Rejection, dated Jun. 12, 2012, 6 pages.
International Patent Application No. PCT/JP2011/001075: International Search Report dated Apr. 26, 2011, 2 pages.
Okamura et al., "Quinoline and Benzimidazole Derivatives: Candidate Probes for In Vivo Imaging of Tau Pathology in Alzheimer's Disease", The Journal of Neuroscience, Nov. 23, 2005, 25(47), 10857-10862.
Ono et al., "Novel Chalcones as Probes for in vivo imaging of β-amyloid plaques in Alzheimer's brains", Bioorganic & Medicinal Chemistry, 2007, 15, 6802-6809.
Ono et al., "Rhodanine and Thiohydantoin Derivatives for Detecting Tau Pathology in Alzheimer's Brains", ACS Chemical Neuroscience, 2011, 2, 269-275.

* cited by examiner

*Primary Examiner* — Kamal Saeed
(74) *Attorney, Agent, or Firm* — Woodcock Washburn LLP

(57) ABSTRACT

The present invention is a compound represented by the following formula (1) or a salt thereof. Furthermore, the present invention is an imaging agent used for imaging a tau protein, the imaging agent containing a compound represented by the formula (1) below or a salt thereof. In the formula (1), $R^3$ is a radioactive iodine.

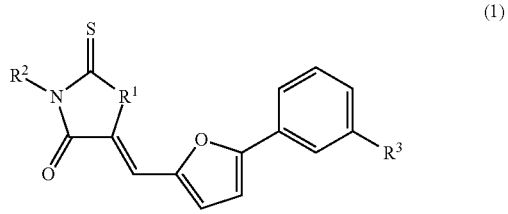

(1)

11 Claims, 11 Drawing Sheets a b

RADIOACTIVE IODINE LABELED ORGANIC COMPOUND OR SALT THEREOF

CROSS-REFERENCE TO RELATED APPLICATIONS

This application is a National Stage of International Application No. PCT/JP2011/001075, filed 24 Feb. 2011, which claims the benefit of Japanese Patent Application No. 2010-061477, filed 1 Mar. 2010the disclosures of which are incorporated herein by reference in their entirety.

TECHNICAL FIELD

The present invention relates to a radioactive iodine-labeled organic compound or a salt thereof.

BACKGROUND ART

Diseases having a common pathological characteristic which a structure having a tau protein aggregate as a main constituent component develops in the brain are called tauopathies. Alzheimer's disease, frontotemporal dementia, Pick's disease, corticobasal degeneration, progressive supranuclear palsy, or the like are known as representative tauopathies.

Tauopathies are often accompanied by serious dementia, which has a large effect on patients and their families. Therefore, it is important to diagnose them at as early a stage as possible. Furthermore, the number of patients affected by these diseases has been increasing in recent years on a background of an aging society, and early diagnosis and therapy therefor have become matters of serious public concern.

As described above, a tau protein aggregate develops in the brain of tauopathy patients, and such a pathological change is thought to have an important role in the symptoms of these diseases. Therefore, much research for the purpose of diagnosis or treatment of a tauopathy has been carried out using an aggregated tau protein as a main target.

So far, various tau protein fibrosis inhibitors including rhodanines have been discovered as compounds having affinity toward a tau protein aggregate (non-patent document 1 and non-patent document 2). Furthermore, various quinoline derivatives and benzimidazole derivatives have been disclosed as biomarkers targeting a tau protein aggregate (non-patent document 3, patent document 1 and patent document 2).

RELATED DOCUMENTS

Patent Documents

Patent document 1: WO2004/054978
Patent document 2: Japanese Patent Application Laid-Open Publication No. 2004-67659

Non-Patent Documents

Non-patent document 1: Kurt R. Brunden et al., "Advances in tau-focused drug discovery for Alzheimer's disease and related tauopathies.", Nature Reviews Drug Discovery, 2009, 8, p. 783-793
Non-patent document 2: Bulic B. et al., "Rhodanine-based tau aggregation inhibitors in cell models of tauopathy.", Angew. Chem. Int. Ed. Engl., 2007, 46, p. 9215-9219
Non-patent document 3: Nobuyuki Okamura, et al., "Quinoline and Benzimidazole Derivatives: Candidate Probes for In Vivo Imaging of Tau Pathology in Alzheimer's Disease.", J. Neurosci., 2005, 25, p. 10857-10862

SUMMARY OF THE INVENTION

Although the above-mentioned various quinoline derivatives, benzimidazole derivatives, and the like have been disclosed as biomarkers targeting a tau protein aggregate, there has been no disclosure of any with clinical application. Furthermore, as described above, various tau protein fibrosis inhibitors including rhodanines have been discovered as compounds having affinity toward a tau protein aggregate. However, further investigation is necessary for use of these compounds as diagnostic imaging agents. In particular, non-invasive imaging requires high selectivity for a tau protein and superior brain delivery properties.

The present invention has been accomplished in light of the above-mentioned circumstances, and it is an object thereof to provide a novel radioactive organic compound having affinity toward a tau protein aggregate, and a tauopathy diagnostic agent containing this compound.

As a result of an investigation, the present inventors have been found that a compound formed by labeling a specific rhodanine or thiohydantoin derivative with a radioactive iodine has affinity toward a tau protein aggregate and has superior brain delivery properties, and the present invention has thus been accomplished.

According to one aspect of the present invention, there is provided a compound represented by the following formula (1) or a salt thereof.

In the above formula (1), $R^1$ is a sulfur atom or a nitrogen atom, $R^2$ is a substituent represented by the following formula (2) or formula (3), and $R^3$ is a radioactive iodine.

According to another aspect of the present invention, there is provided an imaging agent used in imaging of a tau protein, the imaging agent containing a compound represented by the above Formula (1) or a salt thereof.

According to another aspect of the present invention, there is provided an injection containing a compound represented by the above formula (1) or a salt thereof.

According to another aspect of the present invention, there is provided a radioactive iodine labeling precursor containing a compound represented by the following formula (4) or a salt thereof.

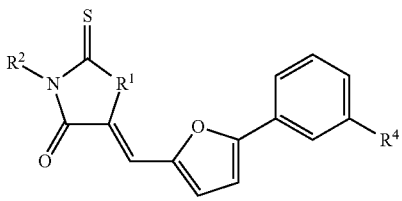

(4)

In the above formula (4), $R^1$ is a sulfur atom or a nitrogen atom, $R^2$ is a substituent represented by the above formula (2) or the above formula (3), and $R^4$ is a trialkylstannyl substituent with alkyl chains having a length of 1 to 4 carbon atoms, a trialkylammonium substituent with alkyl chains having a length of 1 to 4 carbon atoms, or a triphenylstannyl substituent.

According to another aspect of the present invention, there is provided a method for producing a compound represented by the above formula (1) or a salt thereof, the method involving radioiodinating the radioactive iodine labeling precursor.

According to another aspect of the present invention, there is provided an apparatus for producing a compound represented by the above formula (1) or a salt thereof by radioiodinating the radioactive iodine labeling precursor.

According to the present invention, there is provided a radioactive iodine-labeled organic compound having high selectivity for a tau protein and superior brain delivery properties.

BRIEF DESCRIPTION OF THE DRAWINGS

The above-mentioned object, other objects, characteristics, and advantages will become apparent by reference to preferred embodiments described below and the attached drawings.

DESCRIPTION OF EMBODIMENTS

Figure 1:
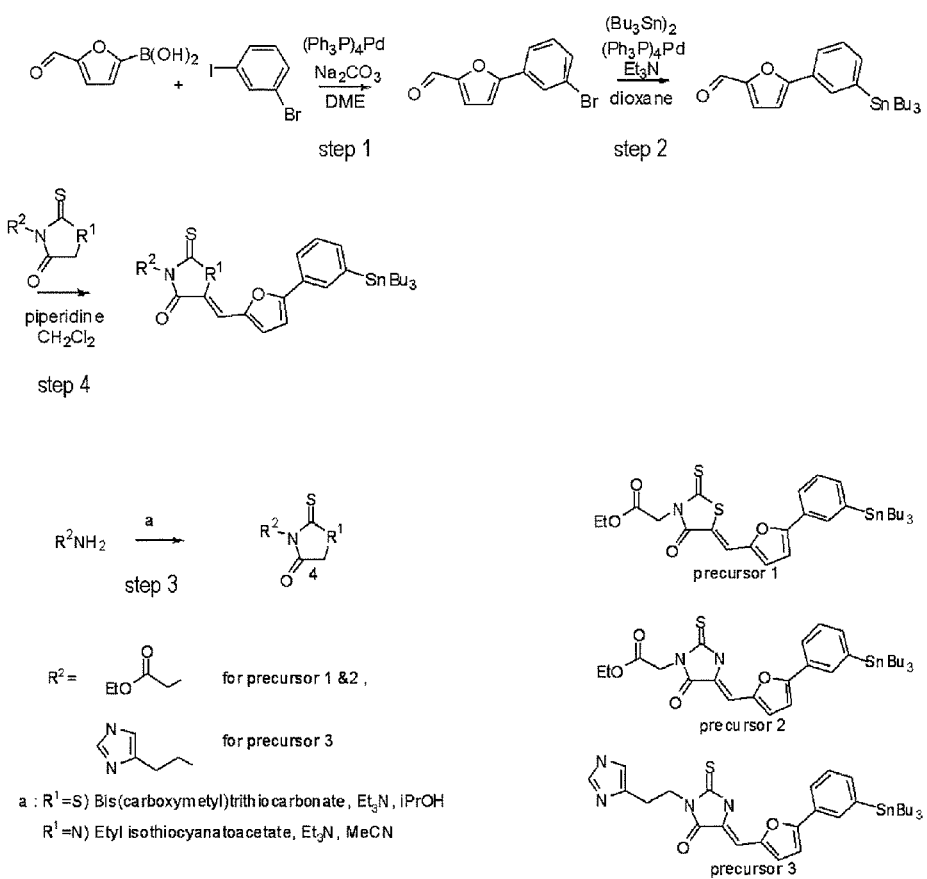
FIG. 1 is an illustration showing a synthetic scheme for a precursor compound of a radioactive iodine-labeled organic compound related to the present invention.

The present invention is a compound represented by the above formula (1) or a salt thereof, and is preferably a rhodanine derivative represented by the following formula (5) or a thiohydantoin derivative represented by the following formula (6).

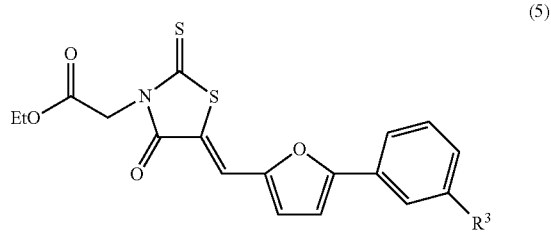

(5)

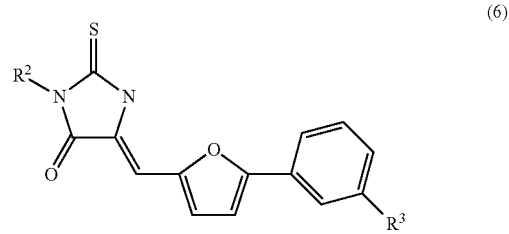

(6)

A compound represented by the formula (5) corresponds to a compound for which in the formula (1) $R^1$ is a sulfur atom and $R^2$ is a substituent represented by the above formula (2).

Furthermore, $R^2$ of the formula (6) is a 2-(4-imidazolyl) ethyl group or an ethoxycarbonylethyl group. A compound represented by the formula (6) having an ethoxycarbonylethyl group as $R^2$ corresponds to a compound represented by the above formula (1) having a nitrogen atom as $R^1$ and a substituent represented by the above formula (2) as $R^2$. Furthermore, a compound represented by the above formula (6) having a 2-(4-imidazolyl)ethyl group as $R^2$ corresponds to a compound represented by the above Formula (1) having a nitrogen atom as $R^1$ and a substituent represented by the above formula (3) as $R^2$.

In the above formulae (1), (5), and (6), $R^3$ is a radioactive iodine. It is not necessary to particularly limit the radioactive iodine, but a radioactive iodine selected from the group consisting of $^{123}I$, $^{124}I$, $^{125}I$, and $^{131}I$ may preferably be used, and more preferably $^{123}I$ may be used. The important point can be that a nuclide that can be used in nuclear medicine diagnostic imaging such as single photon emission computed tomography (SPECT) may be used.

A compound represented by the formula (1) may form a salt, and examples of the salt include acid addition salts such as an inorganic acid salt such as hydrochloride, sulfate, hydrobromide, phosphate, and an organic acid salt such as acetate, trifluoroacetate, succinate, maleate, fumarate, propionate, citrate, tartarate, lactate, oxalate, methanesulfonate, p-toluenesulfonate. Furthermore, a compound represented by the formula (1) or a salt thereof may be a hydrate.

A method for producing a compound represented by the formula (1) or a salt thereof is now explained. A compound represented by the formula (1) or a salt thereof may be obtained by labeling a compound represented by the above formula (4) or a salt thereof with a radioactive iodine. Specifically, a compound represented by the formula (5) may have a compound represented by the following formula (7) or a salt thereof as a radioactive iodine labeling precursor, and a compound represented by the formula (6) may have a compound represented by the following formula (8) or a salt thereof as a radioactive iodine labeling precursor.

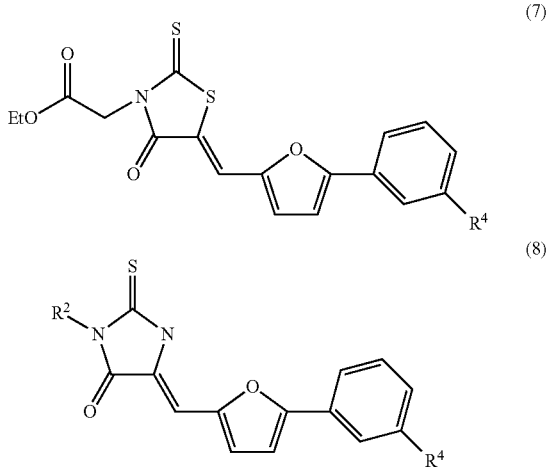

A compound represented by the above formula (7) corresponds to a compound represented by the above formula (4) having a sulfur atom as $R^1$ and a substituent represented by the above formula (2) as $R^2$.

In the formula (8), $R^2$ is a 2-(4-imidazolyl)ethyl group or an ethoxycarbonylethyl group. A compound represented by the above formula (8) having an ethoxycarbonylethyl group as $R^2$ corresponds to a compound of the above formula (4) having a nitrogen atom as $R^1$ and a substituent represented by the above formula (2) as $R^2$. A compound of represented by the above formula (8) having a 2-(4-imidazolyl)ethyl group as $R^2$ corresponds to a compound represented by the above formula (4) having a nitrogen atom as $R^1$ and a substituent represented by the above formula (3) as $R^2$.

In the above formulae (7) and (8), $R^4$ is a trialkylstannyl substituent with alkyl chains having a length of 1 to 4 carbon atoms, a trialkylammonium substituent with alkyl chains having a length of 1 to 4 carbon atoms, or a triphenylstannyl substituent. A trimethylstannyl substituent or a tributylstannyl substituent may preferably be used as the trialkylstannyl substituent for $R^4$. The important point is that it may be a group that can be used in a precursor compound of the radioactive iodine-labeled compound. Since this compound has a functional group represented by $R^4$, it may suitably be used as a precursor of the radioactive iodine-labeled compound related to the present invention.

Method for Synthesizing Precursor Compound of Radioactive Iodine-Labeled Organic Compound A method for synthesizing a precursor compound of a radioactive iodine-labeled organic compound related to one embodiment of the present invention is explained below by reference to the drawings while taking as an example the case of synthesis of (Z)-ethyl-2-(5-oxo-2-thioxo-4-((5-(3-(tributylstannyl)phenyl)furan-2-yl)methylene)imidazolidin-1-yl) acetate (precursor 2 in FIG. 1).

Synthesis of (Z)-ethyl-2-(5-oxo-2-thioxo-4-((5-(3-(tributylstannyl)phenyl)furan-2-yl)methylene)imidazolidin-1-yl) acetate may be carried out in accordance with a known method, for example, a method described in non-patent document 2. First, substantially equivalent amounts of 5-formyl-2-furanboronic acid and 3-bromoiodobenzene are dissolved in 1,2-dimethoxyethane, and sodium carbonate and a catalytic amount of tetrakis(triphenylphosphine)palladium are added thereto. This solution is heated to reflux while stirring so as to carry out a reaction. After the reaction is complete, the solvent is removed by evaporation. Then, purification is carried out to give 5-(3-bromophenyl)furan-2-carbaldehyde (FIG. 1, step 1).

Next, the 5-(3-bromophenyl)furan-2-carbaldehyde is dissolved in 1,4-dioxane, bis(tributyltin) is added thereto, and triethylamine and a catalytic amount of tetrakis(triphenylphosphine)palladium are added thereto. This reaction liquid is heated to reflux while stirring to thus carry out a reaction, and the solvent is removed by evaporation under reduced pressure after the reaction, to give 5-(3-(tributylstannyl)phenyl)furan-2-carbaldehyde (FIG. 1, step 2). In this step, an equivalent or more of bis(tributyltin) with respect to the 5-(3-bromophenyl)furan-2-carbaldehyde may be added.

Separately, substantially equivalent amounts of glycine ethyl ester and ethyl isothiocyanatoacetate are dissolved in acetonitrile, triethylamine is added thereto, and a reaction is carried out while stirring at room temperature (25° C.). After the reaction is completed, the solvent is distilled off, and purification is carried out, thus giving ethyl-2-(5-oxo-2-thioxoimidazolidin-1-yl)acetate (FIG. 1, step 3). This ethyl-2-(5-oxo-2-thioxoimidazolidin-1-yl)acetate and the 5-(3-(tributylstannyl)phenyl)furan-2-carbaldehyde synthesized in step 2 above are dissolved in dichloromethane, piperidine is added thereto, and a reaction is carried out while stirring well at room temperature. After the reaction is completed, the solvent is removed by evaporation. Then, the purification is carried out to give the target (Z)-ethyl-2-(5-oxo-2-thioxo-4-((5-(3-(tributylstannyl)phenyl)furan-2-yl)methylene)imidazolidin-1-yl)acetate (FIG. 1, step 4).

When a compound having a trialkylstannyl substituent other than a tributylstannyl substituent as the substituent at the 3-position of the phenyl is obtained, various bis(trialkyltin)s corresponding to the target may be used instead of the bis(tributyltin) in step 2 of FIG. 1. For example, when a compound having a trimethylstannyl substituent as such a substituent, the same reaction as above may be carried out using bis(trimethyltin) in step 2 of FIG. 1.

When a compound having sulfur atom as substitute for nitrogen atom at the 3-position of the imidazole ring is obtained, a reaction is carried out in the same manner except that bis(carboxymethyl) trithiocarbonate is used instead of ethyl isothiocyanatoacetate, and isopropanol is used as the solvent instead of acetonitrile in step 3 of FIG. 1, and then step 4 of FIG. 1 may be carried out with using the resulting reaction product.

Method for Synthesizing Radioactive Iodine-Labeled Organic Compound

A method for producing a radioactive iodine-labeled organic compound related to another aspect of the present invention is now explained. A radioactive iodine-labeled organic compound related to the present invention may be produced using a production apparatus equipped with at least a reaction vessel, which serves as a reaction location, and the apparatus is preferably equipped with a member that can provide shielding from radiation emitted from the reaction vessel. Synthesis of a radioactive iodine-labeled organic compound related to the present invention may be carried out by dissolving a labeling precursor compound synthesized by the above-mentioned procedure in an inert organic solvent, adding thereto a radioactive iodine-labeled sodium iodide solution or the like obtained by a known method, and adding an acid and an oxidizing agent to thus carry out a reaction. Various solvents having unreactivity with the labeling precursor, sodium iodide, and the like may be used as the inert organic solvent for dissolving the labeling precursor compound, and methanol may preferably be used.

Various acids may be used as the acid, and hydrochloric acid may preferably be used.

The oxidizing agent is not particularly limited as long as it can oxidize iodine in a reaction solution, and hydrogen peroxide or peracetic acid may preferably be used. The amount of oxidizing agent added may be an amount sufficient for oxidizing iodine in the reaction solution.

possible to image a $^{123}$I-labeled compound by using a SPECT apparatus. A tauopathy (a disease due to the accumulation of a tau protein in the brain) may be diagnosed by the image obtained in such a way, and it becomes possible to noninvasively diagnose Alzheimer's disease, frontotemporal dementia, Pick's disease, corticobasal degeneration, progressive supranuclear palsy, and the like.

Modes for carrying out the present invention are described above, but they are only for illustrating the present invention, and various constitutions other than the above may be employed.

EXAMPLES

The present invention is explained in further detail below by reference to Examples, but the present invention is not limited to the contents thereof. The names of the compounds used in the experiments of the Examples below are as defined in Table 1.

TABLE 1

Names of compounds used in Examples

Figure 2:
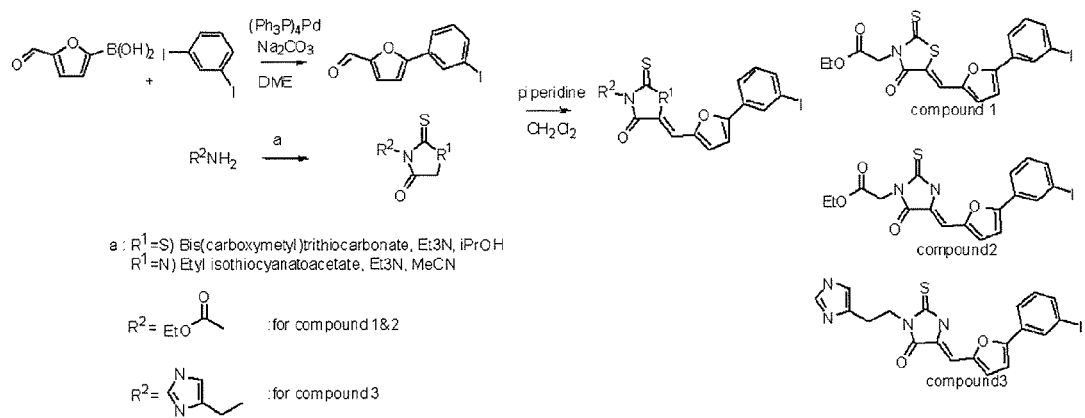
FIG. 2 is an illustration showing a synthetic scheme for a non-radioactive iodine organic compound.

| Compound name (Shown in FIG. 1 and FIG. 2) | Common name |
|---|---|
| Compound 1 | (Z)-Ethyl-2-(5-((5-(3-iodophenyl)furan-2-yl)methylene)-4-oxo-2-thioxothiazolidin-3-yl) acetate (non-radioactive iodinated compound) |
| Compound 2 | (Z)-Ethyl-2-(4-((5-(3-iodophenyl)furan-2-yl)methylene)-5-oxo-2-thioxoimidazolidin-1-yl) acetate (non-radioactive iodinated compound) |
| Compound 3 | (Z)-3-(2-(1H-Imidazol-4-yl)ethyl)-5-((5-(3-iodophenyl) furan-2-yl)methylene)-2-thioxoimidazolidin-4-one (non-radioactive iodinated compound) |
| Labeling precursor 1 (Precursor 1) | (Z)-Ethyl-2-(4-oxo-2-thioxo-5-((5-(3-(tributylstannyl) phenyl)furan-2-yl)methylene)thiazolidin-3-yl) acetate |
| Labeling precursor 2 (Precursor 2) | (Z)-Ethyl-2-(5-oxo-2-thioxo-4-((5-(3-(tributylstannyl) phenyl)furan-2-yl)methylene)imidazolidin-1-yl) acetate |
| Labeling precursor 3 (Precursor 3) | (Z)-3-(2-(1H-Imidazol-4-yl)ethyl)-2-thioxo-5-((5-(3-(tributylstannyl)phenyl)furan-2-yl)methylene)imidazolidin-4-one |
| Radioactive iodine-labeled compound 1 | (Z)-Ethyl-2-(5-((5-(3-($^{125}$I)iodophenyl)furan-2-yl)methylene)-4-oxo-2-thioxothiazolidin-3-yl) acetate |
| Radioactive iodine-labeled compound 2 | (Z)-Ethyl-2-(4-((5-(3-($^{125}$I)iodophenyl)furan-2-yl)methylene)-5-oxo-2-thioxoimidazolidin-l-yl) acetate |
| Radioactive iodine-labeled compound 3 | (Z)-3-(2-(1H-Imidazol-4-yl)ethyl)-5-((5-(3-($^{125}$I)iodophenyl)furan-2-yl)methylene)-2-thioxoimidazolidin-4-one |

Method for Preparing Imaging Agent for Tau Protein Related to the Present Invention and Method for Use Thereof.

An imaging agent for a tau protein related to the present invention may be prepared as a liquid in which a radioactive iodine-labeled organic compound related to the present invention is formulated in water, physiological saline, Ringer solution, or the like that has been adjusted to have an appropriate pH as desired, in the same manner as for other generally known radioactive diagnostic agents. It is necessary for the concentration of the present compound in this case to be no greater than a concentration that can give stability of the present compound that is formulated. The form of administration of the present compound is preferably an injection, and the amount administered is not particularly limited as long as it gives a concentration that is sufficient for imaging of the distribution of the compound that is administered. For example, in the case of an $^{123}$I-labeled compound, about 50 to 600 MBq per adult with a weight of 60 kg may be intravenously or locally administered.

The distribution of the present compound that is administered may be imaged by a known method. For example, it is Example 1

Synthesis of (Z)-ethyl-2-(5-((5-(3-iodophenyl)furan-2-yl)methylene)-4-oxo-2-thioxothiazolidin-3-yl) acetate (non-radioactive iodinated compound) (compound 1)

5-Formyl-2-furanboronic acid (280 mg, 2 mmol) and 1,3-diiodobenzene (660 mg, 2 mmol) were dissolved in 1,2-dimethoxyethane (15 mL), tetrakis(triphenylphosphine)palladium (114 mg, 0.1 mmol) was added thereto, 2 mol/L sodium carbonate (4.6 mL) was then added thereto, and the mixture was heated to reflux for 3 hours while stirring. After the reaction was completed water (20 mL) was added, and extraction with ethyl acetate (20 mL×2) was carried out. The organic layer was washed with saturated brine, water was removed using anhydrous sodium sulfate, the solvent was then removed by evaporation under reduced pressure, and the residue was subjected to silica gel column chromatography using ethyl acetate/hexane (3/7 (volume ratio)) as an eluent, to give 5-(3-iodophenyl)furan-2-carbaldehyde in a yield of 155 mg (yield 25.9%).

Separately, glycine ethyl ester hydrochloride (140 mg, 1 mmol) and bis(carboxymethyl) trithiocarbonate (224 mg, 1 mmol) were dissolved in 2-propanol (6 mL), triethylamine (0.6 mL) was added thereto, and the mixture was heated to reflux for 1 hour while stirring. After the reaction was completed the solvent was removed by evaporation under reduced pressure, and the residue was subjected to silica gel column chromatography using ethyl acetate/hexane (1/1 (volume ratio)) as an eluent, to give ethyl-2-(4-oxo-2-thioxothiazolidin-3-yl)acetate in a yield of 177 mg (yield 80.8%).

5-(3-Iodophenyl)furan-2-carbaldehyde (30 mg, 0.1 mmol) and ethyl-2-(4-oxo-2-thioxothiazolidin-3-yl)acetate (22 mg, 0.1 mmol) were dissolved in dichloromethane (7 mL), piperidine (20 µL) was added thereto, and the mixture was stirred at room temperature (25° C.) for 3 hours. After the reaction was completed the solvent was removed by evaporation under reduced pressure, and the residue was subjected to silica gel column chromatography using ethyl acetate/hexane (3/7 (volume ratio)) as an eluent, to give the target compound 1 in a yield of 38 mg (yield 76.2%).

The results of NMR analysis and mass spectrometry of the obtained compound 1 were as follows. In the present specification, the results of NMR analysis and mass spectrometry show the results of measurement using a JNM400 NMR apparatus made by JEOL and an LCMS-2010 mass spectrometer made by Shimadzu Corporation.

$^1$H NMR (400 MHz, DMSO) 68.25 (s, 1H), 7.88 (d, J=8.0 Hz, 1H), 7.81 (d, J=8.0 Hz, 1H), 7.80 (s, 1H), 7.48 (d, J=4.0 Hz, 1H), 7.43 (d, J=4.0 Hz, 1H), 7.39 (t, J=8.0 Hz, 1H), 4.84 (s, 2H), 4.17 (q, J=7.2 Hz, 2H), 1.21 (t, J=7.2 Hz, 3H)

MS (APCI) m/z 500 [MH$^+$]

Example 2

Synthesis of (Z)-ethyl-2-(4-((5-(3-iodophenyl)furan-2-yl)methylene)-5-oxo-2-thioxoimidazolidin-1-yl)acetate (non-radioactive iodinated compound) (compound 2)

Glycine ethyl ester hydrochloride (140 mg, 1 mmol) and ethyl isothiocyanatoacetate (145 mg, 1 mmol) were dissolved in acetonitrile (6 mL), triethylamine (0.6 mL) was added thereto, and the mixture was stirred at room temperature (25° C.) for 10 minutes. After the reaction was completed the solvent was removed by evaporation under reduced pressure, and the residue was subjected to silica gel column chromatography using ethyl acetate/hexane (1/1 (volume ratio)) as an eluent, to give ethyl-2-(5-oxo-2-thioxoimidazolidin-1-yl)acetate in a yield of 170 mg (yield 84.2%).

5-(3-Iodophenyl)furan-2-carbaldehyde (30 mg, 0.1 mmol) synthesized by the same method as in Example 1 and ethyl-2-(5-oxo-2-thioxoimidazolidin-1-yl)acetate (20 mg, 0.1 mmol) were dissolved in dichloromethane (7 mL), piperidine (20 µL) was added thereto, and the mixture was stirred at room temperature (25° C.) overnight. After the reaction was completed the solvent was removed by evaporation under reduced pressure, and the residue was subjected to silica gel column chromatography using ethyl acetate/hexane (3/7 (volume ratio)) as an eluent, to give compound 2 in a yield of 21 mg (yield 43.6%).

The results of NMR analysis and mass spectrometry of the obtained compound 2 were as follows.

$^1$H NMR (400 MHz, DMSO-d$_6$) δ8.34 (s, 1H), 7.99 (d, J=8.0 Hz, 1H), 7.73 (d, J=8.0 Hz, 1H), 7.38 (d, J=4.0 Hz, 1H), 7.33 (d, J=4.0 Hz, 1H), 7.28 (t, J=8.0 Hz, 1H), 6.68 (s, 1H), 4.61 (s, 2H), 4.17 (q, J=7.2 Hz, 2H), 1.21 (t, J=7.2 Hz, 3H)

MS (APCI) m/z 483 [MH$^+$]

Example 3

Synthesis of (Z)-3-(2-(1H-imidazol-4-yl)ethyl)-5-((5-(3-iodophenyl)furan-2-yl)methylene)-2-thioxoimidazolidin-4-one (non-radioactive iodinated compound) (compound 3)

Histamine (111 mg, 1 mmol) and ethyl isothiocyanatoacetate (145 mg, 1 mmol) were dissolved in acetonitrile (6 mL), and the mixture was stirred at room temperature (25° C.) for 10 minutes. After the reaction was completed the solvent was removed by evaporation under reduced pressure, and the residue was subjected to silica gel column chromatography using chloroform/methanol (4/1 (volume ratio)) as an eluent, to give 3-(2-(1H-imidazol-4-yl)ethyl)-2-thioxoimidazolidin-4-one in a yield of 167 mg (yield 79.5%).

5-(3-Iodophenyl)furan-2-carbaldehyde (30 mg, 0.1 mmol) synthesized by the same method as in Example 1 and 3-(2-(1H-imidazol-4-yl)ethyl)-2-thioxoimidazolidin-4-one (21 mg, 0.1 mmol) were dissolved in dichloromethane (7 mL), piperidine (20 µL) was added thereto, and the mixture was stirred at room temperature (25° C.) for 3 hours. After the reaction was completed the solvent was removed by evaporation under reduced pressure, and the residue was subjected to silica gel column chromatography using chloroform/methanol (9/1 (volume ratio)) as an eluent, to give compound 3 in a yield of 25 mg (yield 51.0%).

The results of NMR analysis and mass spectrometry of the obtained compound 3 were as follows.

$^1$H NMR (400 MHz, DMSO-d$_6$) δ 12.1 (ar, s, 1H), 8.32 (s, 1H), 7.98 (d, J=8.0 Hz, 1H), 7.72 (d, J=8.0 Hz, 1H), 7.58 (s, 1H), 7.35 (d, J=4.0 Hz, 1H), 7.31 (d, J=4.0 Hz, 1H), 7.28 (t, J=8.0 Hz, 1H), 6.86 (s, 1H), 6.55 (s, 1H), 4.02 (t, J=7.6 Hz, 2H), 2.87 (t, J=7.6 Hz, 2H)

MS (APCI) m/z 491 [MH$^+$]

Example 4

Synthesis of (Z)-ethyl-2-(4-oxo-2-thioxo-5-((5-(3-(tributylstannyl)phenyl)furan-2-yl)methylene)thiazolidin-3-yl)acetate (labeling precursor 1)

5-Formyl-2-furanboronic acid (676 mg, 4.8 mmol) and 3-bromoiodobenzene (1132 mg, 4 mmol) were dissolved in 1,2-dimethoxyethane (30 mL), tetrakis(triphenylphosphine)palladium (228 mg, 0.2 mmol) was added thereto, 2 mol/L sodium carbonate (9.6 mL) was further added thereto, and the mixture was heated to reflux for 2 hours while stirring. After the reaction was completed water (20 mL) was added thereto, and extraction with ethyl acetate (20 mL×2) was carried out. The organic layer was washed with saturated brine, water was removed using anhydrous sodium sulfate, the solvent was then removed by evaporation under reduced pressure, and the residue was subjected to silica gel column chromatography using ethyl acetate/hexane (3/7 (volume ratio)) as an eluent, to give 5-(3-bromophenyl)furan-2-carbaldehyde in a yield of 306 mg (yield 25.9%).

5-(3-Bromophenyl)furan-2-carbaldehyde (50 mg, 0.2 mmol) was dissolved in 1,4-dioxane (5 mL), bis(tributyltin) (0.4 mL), tetrakis(triphenylphosphine)palladium (50 mg, 0.04 mmol), and triethylamine (4 mL) were added thereto, and the mixture was heated to reflux for 3 hours while stirring. After the reaction was completed the solvent was removed by evaporation under reduced pressure, and the residue was subjected to silica gel column chromatography using ethyl acetate/hexane (1/9 (volume ratio)) as an eluent, to give 5-(3-(tributylstannyl)phenyl)furan-2-carbaldehyde in a yield of 37 mg (yield 40%).

5-(3-(Tributylstannyl)phenyl)furan-2-carbaldehyde (7 mg, 0.015 mmol) and ethyl-2-(4-oxo-2-thioxothiazolidin-3-yl)acetate (3.5 mg, 0.016 mmol) synthesized by the same method as in Example 1 were dissolved in dichloromethane (2 mL), piperidine (5 µL) was added thereto, and the mixture was stirred at room temperature (25° C.) overnight. After the reaction was completed the solvent was removed by evaporation under reduced pressure, and the residue was subjected to silica gel column chromatography using ethyl acetate/hexane (3/7 (volume ratio)) as an eluent, to give labeling precursor 1 in a yield of 6 mg (yield 56.6%).

Example 5

Synthesis of (Z)-ethyl-2-(5-oxo-2-thioxo-4-((5-(3-(tributylstannyl)phenyl)furan-2-yl)methylene)imidazolidin-1-yl)acetate (labeling precursor 2)

5-(3-(Tributylstannyl)phenyl)furan-2-carbaldehyde (10 mg, 0.022 mmol) synthesized by the same method as in Example 4 and ethyl-2-(5-oxo-2-thioxoimidazolidin-1-yl)acetate (4.4 mg, 0.022 mmol) synthesized by the same method as in Example 2 were dissolved in dichloromethane (3 mL), piperidine (5 µL) was added thereto, and the mixture was stirred at room temperature (25° C.) overnight. After the reaction was completed the solvent was removed by evaporation under reduced pressure, and the residue was subjected to silica gel column chromatography using ethyl acetate/hexane (3/7 (volume ratio)) as an eluent, to give labeling precursor 2 in a yield of 11 mg (74.0%).

Example 6

Synthesis of (Z)-3-(2-(1H-imidazol-4-yl)ethyl)-2-thioxo-5-((5-(3-(tributylstannyl)phenyl)furan-2-yl)methylene)imidazolidin-4-one (labeling precursor 3)

5-(3-(Tributylstannyl)phenyl)furan-2-carbaldehyde (65 mg, 0.14 mmol) synthesized by the same method as in Example 4 and 3-(2-(1H-imidazol-4-yl)ethyl)-2-thioximidazolidin-4-one (32 mg, 0.15 mmol) synthesized by the same method as in Example 3 were dissolved in dichloromethane (7 mL), piperidine (20 µL) was added thereto, and the mixture was stirred at room temperature (25° C.) overnight. After the reaction was completed the solvent was removed by evaporation under reduced pressure, and the residue was subjected to silica gel column chromatography using chloroform/methanol (9/1 (volume ratio)) as an eluent, to give labeling precursor 3 in a yield of 42 mg (yield 45.9%).

Example 7

Synthesis of $^{125}$I Labeled Form

Ethanol solutions (1 mg/mL) (50 µL) of labeling precursors 1 to 3 synthesized in Examples 4 to 6 were prepared, Na[$^{125}$I] (3.7-7.4 MBq (0.1-0.2 mCi)) was added thereto, and 1 mol/L hydrochloric acid (50 µL) and 3 vol % $H_2O_2$ aqueous solution (50 µL) were added thereto. After a reaction was carried out at room temperature (25° C.) for 5 minutes, the reaction was quenched by adding a saturated sodium bisulfite aqueous solution (100 µL) as a reducing agent. After the reaction liquid was neutralized by adding a saturated sodium bicarbonate aqueous solution (100 µL), the target product was extracted with ethyl acetate. Water was removed from the product by passing it through a column charged with anhydrous sodium sulfate, and the solvent was then evaporated off by nitrogen gas. $^{125}$I-labeled ligands were purified by means of reverse phase HPLC (mobile phase (volume ratio); water:acetonitrile=3:7 for radioactive iodine-labeled compound 1, water:acetonitrile=4:6 for radioactive iodine-labeled compound 2, water:methanol=25:75 for radioactive iodine-labeled compound 3) using the corresponding non-radioactive compounds as controls. Radioactive iodine-labeled compounds 1, 2, and 3 were obtained at a radiochemical yield of 8% to 22% and a radiochemical purity of at least 90%.

Example 8

Radioactivity Biodistribution Experiment in Normal Mouse

Radioactive iodine-labeled compounds 1 to 3 were diluted with physiological saline containing 10% ethanol to give sample solutions. Each of the sample solutions containing radioactive iodine-labeled compounds 1 to 3 was administered to a group of five 5-week-old ddY mice (male 26-28 g) via the tail vein (6.66-18.5 kBq (0.18-0.5 µCi) per each mice) (100 µL). Mice were decapitated after 2, 10, 30, and 60 minutes, and then each organ was then removed after blood collection, and radiation counts were measured in a γ counter. In the present specification, measurement by a γ counter was carried out using a PerkinElmer WIZARD$^3$480.

The results are shown in Tables 2 to 4. Table 2 shows the results of radioactive iodine-labeled compound 1. Table 3 shows the results of radioactive iodine-labeled compound 2. Table 4 shows the results of radioactive iodine-labeled compound 3. As shown in Tables 2 to 4, it was confirmed that each radioactive iodine-labeled compound moved quickly into the brain after administration.

TABLE 2

Amount of radioactivity in each organ at different times after administering radioactive iodine-labeled compound 1

| % ID/g | 2 minutes | 10 minutes | 30 minutes | 60 minutes |
|---|---|---|---|---|
| Blood | 6.70 ± 0.53 | 3.58 ± 0.37 | 2.27 ± 0.44 | 1.59 ± 0.14 |
| Brain | 0.23 ± 0.02 | 0.16 ± 0.01 | 0.15 ± 0.03 | 0.11 ± 0.02 |
| Spleen | 6.70 ± 0.54 | 4.11 ± 0.80 | 2.66 ± 0.84 | 1.94 ± 0.40 |
| Pancreas | 1.74 ± 0.19 | 1.75 ± 0.18 | 1.16 ± 0.17 | 0.73 ± 0.08 |
| Stomach | 0.75 ± 0.17 | 1.53 ± 0.44 | 3.65 ± 0.78 | 4.51 ± 0.38 |
| Intestine | 1.77 ± 0.33 | 7.97 ± 1.24 | 15.1 ± 1.82 | 21.0 ± 2.73 |
| Kidney | 8.50 ± 0.83 | 7.64 ± 0.69 | 6.42 ± 1.17 | 3.91 ± 0.18 |
| Liver | 43.1 ± 2.07 | 29.5 ± 2.17 | 14.7 ± 2.27 | 11.3 ± 0.87 |
| Heart | 9.41 ± 0.49 | 5.05 ± 0.39 | 2.38 ± 0.38 | 1.39 ± 0.19 |
| Lung | 13.6 ± 1.00 | 4.44 ± 0.52 | 2.31 ± 0.46 | 1.56 ± 0.22 |

TABLE 3

Amount of radioactivity in each organ at different times after administering radioactive iodine-labeled compound 2

| % ID/g | 2 minutes | 10 minutes | 30 minutes | 60 minutes |
|---|---|---|---|---|
| Blood | 9.49 ± 0.82 | 2.38 ± 0.88 | 1.79 ± 0.11 | 1.50 ± 0.10 |
| Brain | 0.57 ± 0.07 | 0.32 ± 0.02 | 0.18 ± 0.02 | 0.10 ± 0.03 |
| Spleen | 9.16 ± 2.04 | 12.2 ± 2.28 | 13.6 ± 4.29 | 10.0 ± 2.49 |
| Pancreas | 1.79 ± 0.27 | 0.98 ± 0.08 | 0.56 ± 0.10 | 0.45 ± 0.08 |
| Stomach | 0.93 ± 0.36 | 3.39 ± 3.03 | 3.39 ± 2.98 | 5.32 ± 2.68 |
| Intestine | 1.85 ± 0.26 | 7.88 ± 1.46 | 17.7 ± 2.22 | 23.4 ± 5.37 |
| Kidney | 9.21 ± 0.68 | 9.11 ± 1.15 | 3.86 ± 0.85 | 2.68 ± 0.75 |
| Liver | 32.2 ± 1.67 | 32.1 ± 2.09 | 22.6 ± 3.42 | 20.2 ± 1.93 |

TABLE 3-continued

Amount of radioactivity in each organ at different times after administering radioactive iodine-labeled compound 2

| % ID/g | 2 minutes | 10 minutes | 30 minutes | 60 minutes |
|---|---|---|---|---|
| Heart | 7.02 ± 1.23 | 2.05 ± 0.29 | 1.19 ± 0.39 | 1.44 ± 0.39 |
| Lung | 10.8 ± 1.28 | 3.89 ± 0.32 | 2.09 ± 0.43 | 1.70 ± 0.45 |

TABLE 4

Amount of radioactivity in each organ at different times after administering radioactive iodine-labeled compound 3

| % ID/g | 2 minutes | 10 minutes | 30 minutes | 60 minutes |
|---|---|---|---|---|
| Blood | 8.16 ± 1.21 | 2.77 ± 0.21 | 2.11 ± 0.28 | 1.48 ± 0.27 |
| Brain | 1.54 ± 0.10 | 1.30 ± 0.12 | 0.66 ± 0.08 | 0.25 ± 0.02 |
| Spleen | 9.23 ± 0.63 | 10.9 ± 2.78 | 8.51 ± 2.68 | 8.46 ± 2.57 |
| Pancreas | 3.30 ± 0.86 | 2.15 ± 0.23 | 1.15 ± 0.18 | 0.86 ± 0.08 |
| Stomach | 1.33 ± 0.25 | 2.67 ± 1.59 | 4.55 ± 1.28 | 7.45 ± 5.07 |
| Intestine | 2.55 ± 0.16 | 7.41 ± 1.21 | 17.3 ± 1.67 | 23.6 ± 2.39 |
| Kidney | 12.5 ± 0.76 | 7.34 ± 0.70 | 4.97 ± 0.71 | 3.37 ± 0.30 |
| Liver | 35.0 ± 2.27 | 33.3 ± 1.41 | 27.2 ± 2.05 | 22.8 ± 2.13 |
| Heart | 8.48 ± 0.97 | 2.78 ± 0.19 | 1.73 ± 0.18 | 1.30 ± 0.37 |
| Lung | 11.4 ± 1.55 | 4.39 ± 0.42 | 3.00 ± 0.27 | 2.03 ± 0.14 |

Example 9

Competitive Inhibition Experiment Using Thioflavin S (ThS) as ligand

Tau-441 expression vector (provided by Graduate School of Medicine, Osaka City University) was transferred to *E. coli* (BL21), culturing was carried out, and a tau protein was extracted and purified. Heparin (0.1 mg/mL) was added to the purified tau protein (1 mg/mL), and incubation in a 50 mmol/L MES buffer (pH 6.8, 100 mmol/L sodium chloride, 0.5 mmol/L EGTA) at 37° C. was carried out for 3 days, thus preparing an aggregate. Formation of the tau protein aggregate was confirmed by SDS-PAGE and thioflavin S fluorescence assay.

A mixed solution (550 µL) of the tau protein aggregate (final concentration 0.2 mmol/L) thus prepared, thioflavin S (Sigma Aldrich, final concentration 1.5 µmol/L), and compound 1, compound 2, or compound 3 solution at various concentrations (each having final concentrations of 0 to 2.7 µmol/L) was incubated for 30 minutes, and fluorescence spectra at an excitation wavelength of 440 nm were measured using a fluorescence spectrometer (RF-5300PC, Shimadzu Corporation).

Figure 3:
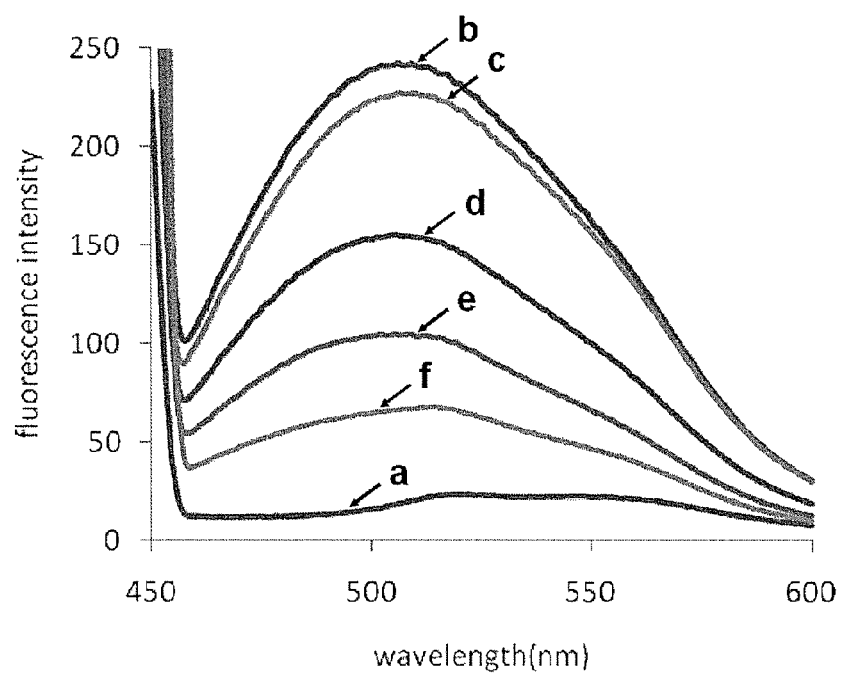
FIG. 3 is a chart showing the results of a competitive inhibition experiment with compound 1 using thioflavin S as a ligand.
Figure 4:
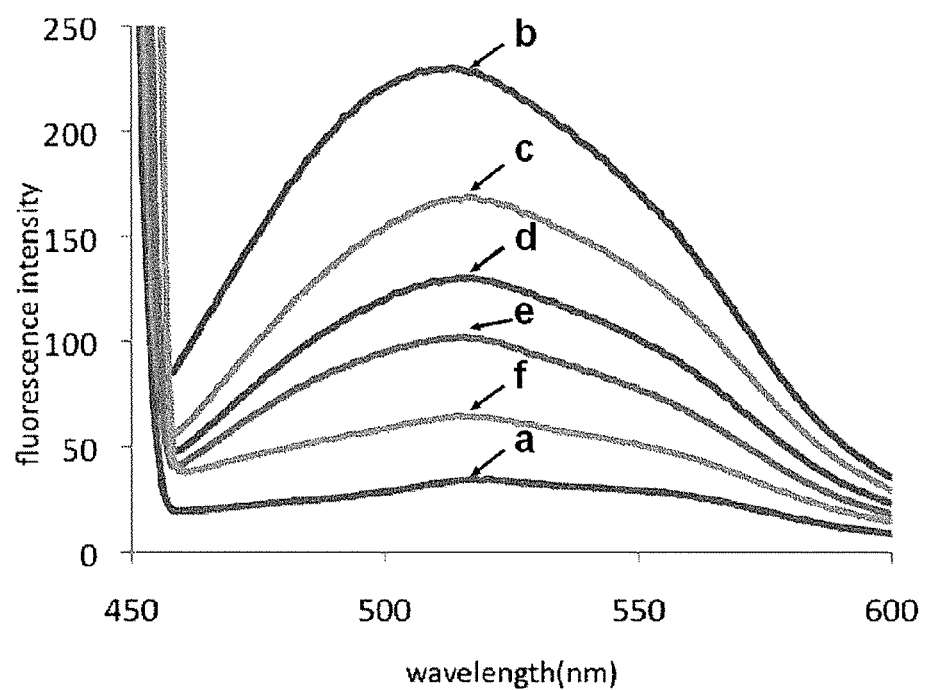
FIG. 4 is a chart showing the results of a competitive inhibition experiment with compound 2 using thioflavin S as a ligand.
Figure 5:
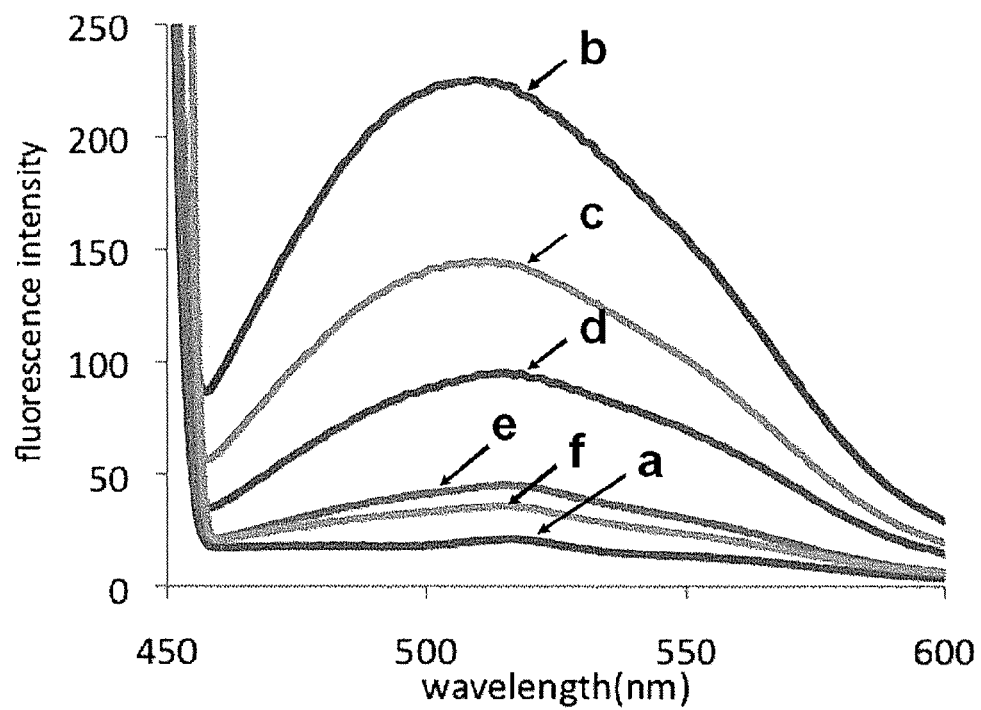
FIG. 5 is a chart showing the results of a competitive inhibition experiment with compound 3 using thioflavin S as a ligand.

The results are shown in FIGS. 3 to 5. In FIGS. 3 to 5, a is a fluorescence spectrum of a sample (sample I) containing only thioflavin S at 1.5 µmol/L, and b is a fluorescence spectrum of a sample (sample II) that is 0.2 µmol/L of the tau protein aggregate in sample I. In FIG. 3, c is a fluorescence spectrum of a sample that is 0.1 µmol/L of compound 1 in sample II, d is a fluorescence spectrum of a sample that is 0.3 µmol/L of compound 1 in sample II, e is a fluorescence spectrum of a sample that is 0.9 µmol/L of compound 1 in sample II, and f is a fluorescence spectrum of a sample that is 2.7 µmol/L of compound 1 in sample II. In FIG. 4, c is a fluorescence spectrum of a sample that is 0.1 µmol/L of compound 2 in sample II, d is a fluorescence spectrum of a sample that is 0.3 µmol/L of compound 2 in sample II, e is a fluorescence spectrum of a sample that is 0.9 µmol/L of compound 2 in sample II, and f is a fluorescence spectrum of a sample that is 2.7 µmol/L of compound 2 in sample II. In FIG. 5, c is a fluorescence spectrum of a sample that is 0.1 µmol/L of compound 3 was added to sample II, d is a fluorescence spectrum of a sample that is 0.3 µmol/L of compound 3 in sample II, e is a fluorescence spectrum of a sample that is 0.9 µmol/L of compound 3 in sample II, and f is a fluorescence spectrum of a sample that is 2.7 µmol/L of compound 3 in sample II. It is clear from FIGS. 3 to 5 that it was confirmed that there was inhibition of binding of a tau protein aggregate to thioflavin S accompanying increasing concentration of compound 1, compound 2, and compound 3 regarding each sample. The results suggest that compound 1, compound 2, and compound 3 have the property of binding to a tau protein aggregate.

Example 10

Tau Protein Binding Experiment Using Size Exclusion Chromatography

Mixed solutions of a tau protein aggregate (final concentration 0.37 µmol/L, prepared in Example 9) or an non-aggregated tau protein (final concentration 0.37 µmol/L) and radioactive iodine-labeled compound 1 (2.0 kBq (0.055 µCi)), radioactive iodine-labeled compound 2 (20 kBq (0.55 µCi)) or radioactive iodine-labeled form 3 (2.0 kBq (0.055 µCi)) were incubated for 1 hour to 1.5 hours, and then subjected to size exclusion chromatography (PD-10 column (GE Healthcare Japan), eluent: phosphate buffered-saline (PBS)). Subsequently, the radioactivity of an eluted fraction of the tau protein aggregate or the non-aggregated tau protein was measured in a γ counter.

As a control, the same experiment was carried out using mixed solutions of PBS buffer and radioactive iodine-labeled compound 1 (2.0 kBq (0.055 µCi)), radioactive iodine-labeled compound 2 (2.0 kBq (0.055 µCi)) or radioactive iodine-labeled compound 3 (2.0 kBq (0.055 µCi)), and then the radioactivity of the same fractions as those in which the tau protein aggregate had been eluted in the above-mentioned experiment was measured in a γ counter.

Figure 6:
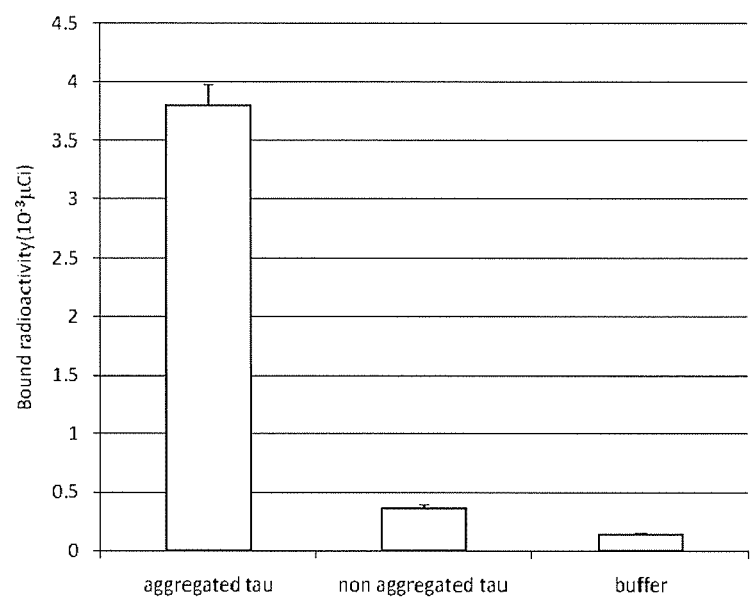
FIG. 6 is a graphic showing the results of a tau protein aggregate binding experiment with radioactive iodine-labeled compound 1.
Figure 7:
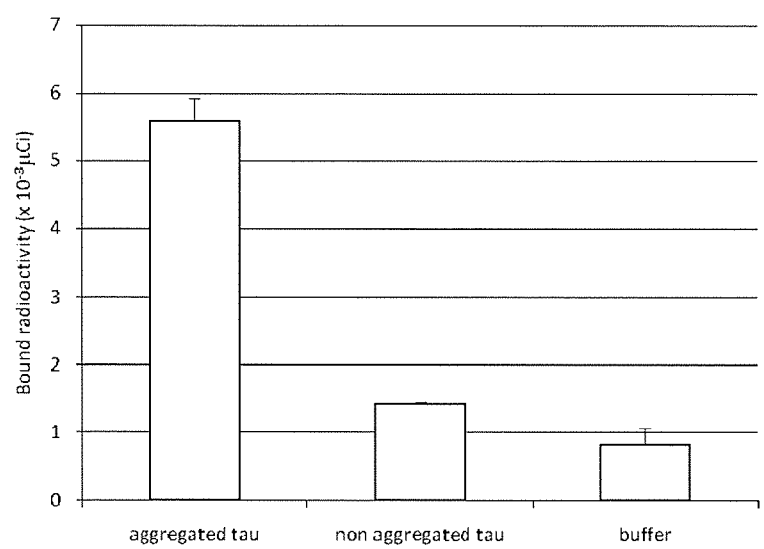
FIG. 7 is a graphic showing the results of a tau protein aggregate binding experiment with radioactive iodine-labeled compound 2.
Figure 8:
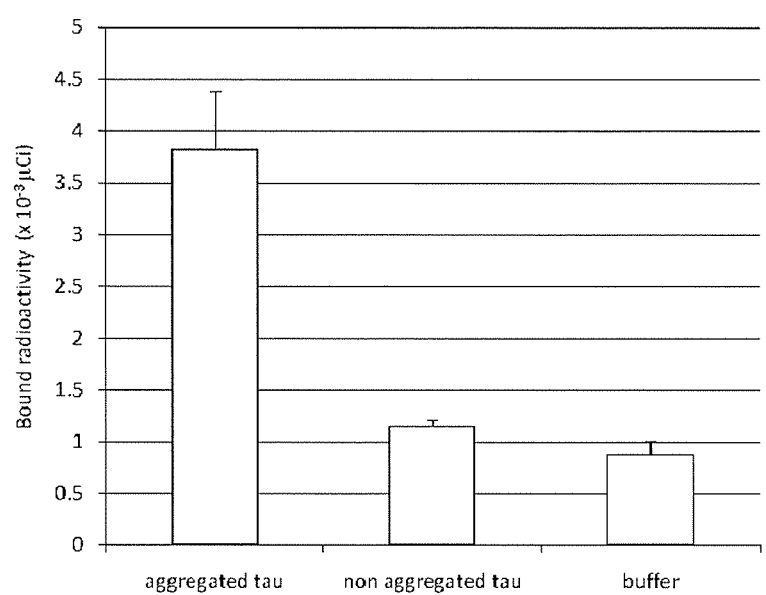
FIG. 8 is a graphic showing the results of a tau protein aggregate binding experiment with radioactive iodine-labeled compound 3.

The results are shown in FIGS. 6 to 8. FIG. 6 is a graphic showing the results using radioactive iodine-labeled compound 1. FIG. 7 is a graphic showing the results using radioactive iodine-labeled compound 2. FIG. 8 is a graphic showing the results using radioactive iodine-labeled compound 3. In FIGS. 6 to 8, the radioactivity of a fraction of the tau protein aggregate is shown as 'aggregated tau', the radioactivity of a fraction with eluted non-aggregated tau protein is shown as 'non aggregated tau', and the radioactivity of a control is shown as 'buffer'. As can be seen in these figures, it was shown that radioactive iodine-labeled compound 1, radioactive iodine-labeled compound 2, and radioactive iodine-labeled compound 3 have the property of specifically binding to a tau protein aggregate.

In Example 8, it can be seen that radioactive iodine-labeled compounds 1 to 3 all have the property of moving quickly into the brain after being intravenously administered. Taking this result into consideration as well, the radioactive iodine-labeled organic compound related to the present invention is thought to have the property of moving into the brain at an early stage after intravenous administration and binding to a tau protein aggregate. Therefore, it is suggested that the radioactive iodine-labeled organic compound related to the present invention enables an aggregate of a phosphorylated tau protein accumulated in the brain to be visualized as a nuclear medicine image.

Example 11

Evaluation Experiment of Binding to Amyloid β

0.5 mg of Aβ (1-42) peptide (purchased from Peptide Institute, Inc.) was dissolved in 2 mL of a PBS buffer containing 1 mmol/L of EDTA and incubated at 37° C. for 42 hours, thus preparing an Aβ42 aggregate. A glass tube was charged with a 10 vol % ethanol aqueous solution (900 μL), Aβ42 aggregate (50 μL, final concentration 30 nmol/L), and radioactive iodine-labeled compound 1, radioactive iodine-labeled compound 2, or radioactive iodine-labeled compound 3 (each 50 μL, 0.018-0.097 μCi), and incubation was carried out for 3 hours. B/F separation was carried out using a cell harvester (Brandel, M-24), and the radioactivity on the filter was measured in a γ counter. The proportion (%) of the radioactivity count on the filter relative to the radioactivity count of each sample used was determined, and binding of each compound to the Aβ42 aggregate was evaluated.

As a control, 4-dimethylamino-4'-iodochalcone (hereinafter, called a chalcone derivative) was prepared in accordance with a method described in the literature (Ono et al., Bioorg Med Chem, 15, 6802-6809, 2007), and the same experiment was carried out (radioactivity count in sample: 0.85-0.37 kBq (0.023-0.01 μCi)).

Figure 9:
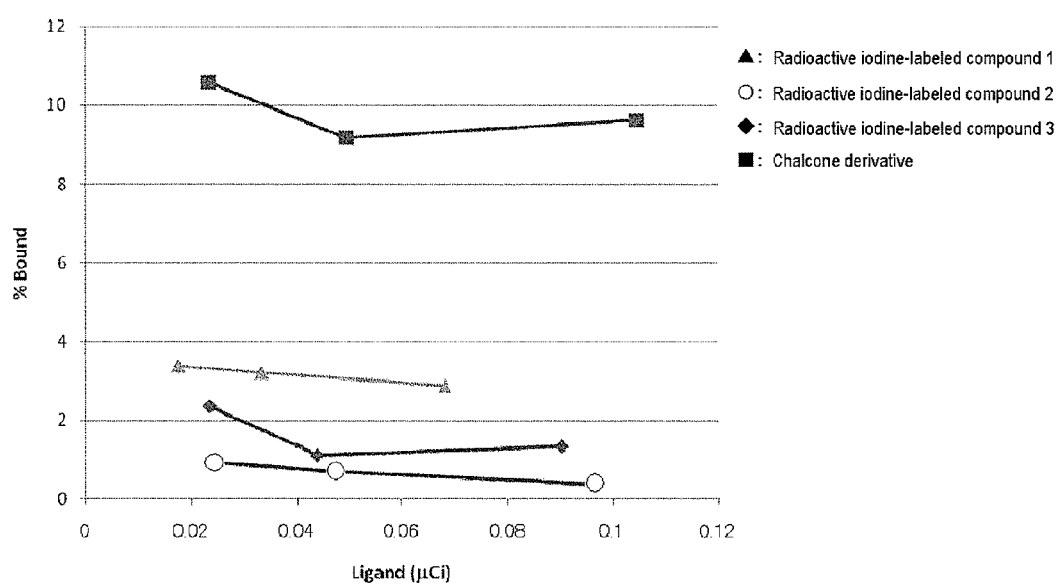
FIG. 9 is a graphic showing the results of evaluation of binding of radioactive iodine-labeled compounds 1, 2, and 3 to an amyloid β aggregate.

FIG. 9 shows the results. As shown in this figure, the chalcone derivative used as a control exhibited binding to the Aβ42 aggregate, but binding of radioactive iodine-labeled compound 1, radioactive iodine-labeled compound 2, and radioactive iodine-labeled compound 3 to the Aβ42 aggregate was significantly lower. Together with Examples 9 and 10 above, this result suggests that the compound related to the present invention has specific binding to a tau protein aggregate.

Example 12

In Vitro Autoradiography Experiment Using Alzheimer's Disease Patient-Derived Brain Slice A postmortem brain slice (paraffin-embedded slice) of the hippocampus of an Alzheimer's disease patient was purchased from BioChain. The brain slice was deparaffinized, a 10% ethanol-containing PBS solution (3.07 kBq/mL (0.083 μCi/mL)) of radioactive iodine-labeled compound 3 was added thereto, and a reaction was carried out for 1 hour. Subsequently, the sample was washed in sequence with a saturated lithium carbonate 50 vol % ethanol aqueous solution (2 minutes×2), a 50 volt ethanol aqueous solution (2 minutes×2), and purified water (30 seconds×2). The sample was exposed to light on an imaging plate for 48 hours, and analyzed using a bioimaging analyzer (model: BAS-5000, Fuji Photo Film Co., Ltd.). Furthermore, an adjacent slice was stained by an anti-phosphorylated tau protein antibody (AT8, Thermo).

Figure 10:
FIG. 10 is a view showing imaging of a tau protein using a brain slice of an Alzheimer's disease patient. (a) is a view showing the result of autoradiography with radioactive iodine-labeled compound 3, and (b) is a view showing the result of staining using an anti-phosphorylated tau protein antibody.
Figure 10:
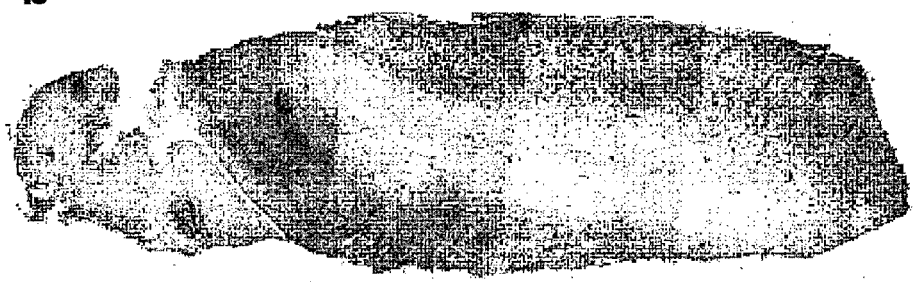

The results are shown in FIG. 10. The radioactivity distribution (FIG. 10a) of radioactive iodine-labeled compound 3 coincided with the distribution (FIG. 10b) of the phosphorylated tau protein observed in the antibody stained slice. This result shows that radioactive iodine-labeled compound 3 has the property of binding to a phosphorylated tau protein in the brain.

In Example 8, it was shown that radioactive iodine-labeled compounds 1 to 3 all have the property of moving quickly into the brain after being intravenously administered. Taking this result into consideration, it is thought that the compound related to the present invention has the property of moving into the brain at an early stage after intravenous administration and binding to a phosphorylated tau protein aggregate. Therefore, it is suggested that the radioactive iodine-labeled organic compound related to the present invention enables an aggregate of a phosphorylated tau protein accumulated in the brain to be visualized as a nuclear medicine image.

Example 13

Inhibition Constant Toward Tau Protein and β Amyloid

First, the dissociation constant ($K_d$) of thioflavin S used as a competitive ligand was first determined by a saturation experiment in order to calculate inhibition constants of compounds 1 to 3. That is, a mixed solution of a 10 vol % ethanol aqueous solution of thioflavin S (0.1-12.8 μmol/L) and the tau protein aggregate (final concentration 0.2 μmol/L, prepared in Example 9) or the Aβ42 aggregate (final concentration 2.2 μmol/L, prepared in Example 11) was incubated for 30 minutes, and the fluorescence intensity was measured using a fluorescence plate reader (FLEX STATION, Molecular Devices). The fluorescence intensity was measured at Ex 440 nm and Em 510 nm for the tau protein aggregate and Ex 440 nm and Em 490 nm for the Aβ42 aggregate. A saturation curve was prepared using GraphPad Prism, and the $K_d$ value for thioflavin S was calculated.

Next, a mixed solution of a 10 volt ethanol aqueous solution of thioflavin S (1.5 μmol/L) and a test compound (0.6 nmol/L to 10 μmol/L) together with the tau protein aggregate (final concentration 0.2 μmol/L, prepared in Example 9) or the Aβ42 aggregate (final concentration 10 μg/ml, prepared in Example 11) was incubated for 30 minutes. Then, the fluorescence intensities at Ex 440 nm and Em 510 nm for the tau protein aggregate and Ex 440 nm and Em 490 nm for the Aβ42 aggregate were measured using a fluorescence plate reader (FLEX STATION, Molecular Devices). GraphPad Prism inhibition curves were prepared, and $K_i$ values of compounds 1 to 3 were determined using the above obtained $K_d$ value of thioflavin S.

The results are shown in Table 5. A competitive inhibition experiment using thioflavin S, which is a β sheet binding fluorescent agent, as a ligand was carried out in order to evaluate the binding of the synthesized rhodanine and thiohydantoin derivatives to the tau protein aggregate. In the results, the rhodanine and thiohydantoin derivatives inhibited binding of thioflavin S to the tau protein aggregate, and the Ki values (Tau in Table 5) of compounds 1, 2, and 3 were 489, 155, and 64 nmol/L respectively. Such results suggest that and these derivatives had high binding to the tau protein aggregate. Subsequently, the same inhibition experiment was carried out using the Aβ42 aggregate, which has the same kind of β sheet structure as the tau protein aggregate. In the results, the Ki values (Aβ42 in Table 5) of compounds 1, 2, and 3 were 752, 864, and 469 nmol/L respectively, and all the derivatives showed high binding to the tau protein aggregate compared with the Aβ42 aggregate. These results suggest that the present derivatives specifically bind to the tau protein aggregate.

TABLE 5

| Compounds | $K_i$ (nM)$^a$ Tau | $K_i$ (nM)$^a$ Aβ42 | $K_i$ ratios of Aβ42/Tau |
|---|---|---|---|
| 1 | 489 ± 62 | 752 ± 128 | 1.54 |
| 2 | 155 ± 14 | 864 ± 147 | 5.57 |
| 3 | 64 ± 7 | 469 ± 60 | 7.33 |

Example 14

Evaluation of Binding to Human Brain Neurofibrillary Tangles Using Alzheimer's Disease Patient-Derived Brain Slice A fluorescent staining experiment with compound 3 using an Alzheimer's disease patient brain slice was carried out in order to evaluate binding to human brain neurofibrillary tangles. A postmortem brain slice (paraffin-embedded slice) of an Alzheimer's disease patient purchased from BioChain was washed with xylene (5 minutes×twice), ethanol, ethanol, a 95 vol % ethanol aqueous solution, an 85 volt ethanol aqueous solution, and a 70 vol % ethanol aqueous solution (1 minute×once) to thus carry out deparaffinization. Subsequently, it was treated in sequence with a 0.3 wt % potassium permanganate aqueous solution (20 minutes×once), PBS (phosphoric acid buffer physiological saline) (2 minutes× twice), a 1 wt % potassium metabisulfite aqueous solution/1 wt % oxalic acid aqueous solution (1 minute×once), PBS (2 minutes×twice), a 1 wt % sodium borohydride aqueous solution (5 minutes×once), and PBS (2 minutes×twice) in order to remove self-fluorescence of the slice. Blocking using 3 wt % BSA-containing PBS/0.1 wt % tritonX100-containing PBS was carried out for 3 hours. Then, a test compound (200 μmol/L/50 vol % ethanol aqueous solution) and the slice were incubated for 1 hour. The slice was washed with 50 vol % ethanol, and examined using a fluorescence microscope. Furthermore, the same slice was stained using thioflavin S (0.125 wt %, 50 vol % ethanol aqueous solution) for 10 minutes. Subsequently, immunostaining using an anti-phosphorylated tau protein antibody (AT8) was carried out. Activation of antigen was carried out in a 0.01 mol/L citric acid buffer in an autoclave (121° C., 2 atm) for 15 minutes. After being immersed in PBS-Tween20 for 2 minutes, the sample was reacted with 3 wt % BSA-containing PBS/0.1 wt % tritonX100-containing PBS at room temperature (25° C.) for 1 hour, and reacted with an AT8 antibody solution (Thermo Scientific) at room temperature (25° C.) overnight. After being washed with PBS-Tween20 for 2 minutes×three times, the sample was reacted with anti-mouse IgG (H+L), rabbit, and biotin-binding solution (VECTOR Laboratories) at room temperature (25° C.) for 1 hour. Subsequently, the sample was reacted with a streptavidin biotin peroxidase complex solution (VECTOR Laboratories), which had been washed with PBS-Tween20 for 2 minutes×three times, at room temperature (25° C.) for 1 hour. After being washed with PBS-Tween20 for 2 minutes×three times, the sample was reacted with a diaminobenzidine solution (Tris buffer) at room temperature (25° C.) for 1 minute. The reaction was quenched by washing with distilled water for 1 minute. After encapsulating, the sample was examined using a microscope.

Figure 11:
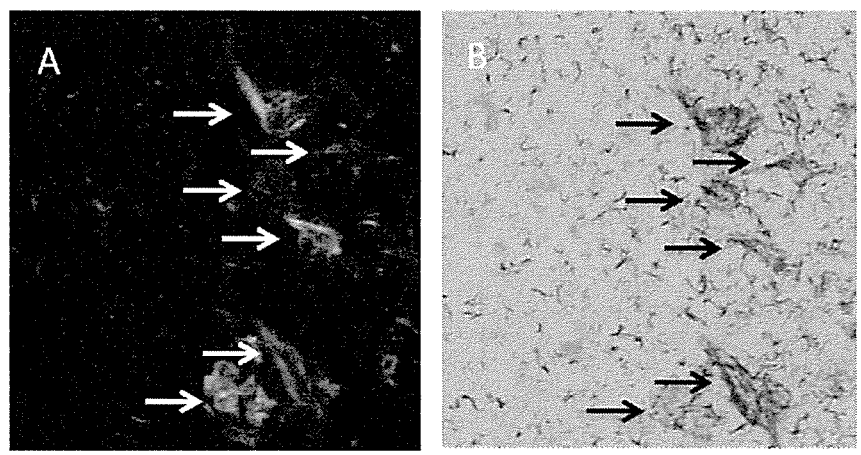
FIG. 11 is a view showing the results of staining of a brain slice of an Alzheimer's disease patient. A is a view showing the result of fluorescent staining using compound 3, and B is a view showing the result of staining using an anti-phosphorylated tau protein antibody.

The results are shown in FIG. 11. Prominent fluorescence accumulation of compound 3 was observed in an anti-phosphorylated tau protein antibody (AT8) immunostaining positive site of the brain slice. It is clear from this result that compound 3 has the property of binding to a tau protein aggregate accumulated in the human brain. FIG. 11A is a view showing the result of fluorescent staining by compound 3, and FIG. 11B is a view showing the result of staining by anti-phosphorylated tau protein antibody.

Industrial Applicability

The compound and tauopathy diagnostic agent related to the present invention can be used in the field of radioactive pharmaceutical product production.

The invention claimed is:

1. A compound represented by the following formula (1) or a salt thereof,

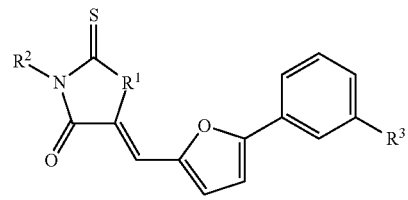

wherein, in the formula (1), $R^1$ is a sulfur atom or a nitrogen atom, $R^2$ is a substituent represented by the following formula (2),

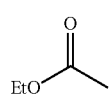

or the following formula (3),

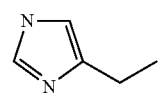

and $R^3$ is a radioactive iodine.

2. The compound or salt thereof according to claim 1, wherein in the formula (1) $R^1$ is a sulfur atom and $R^2$ is a substituent represented by the formula (2).

3. The compound or salt thereof according to claim 1, wherein in the formula (1) $R^1$ is a nitrogen atom and $R^2$ is a substituent represented by the formula (2).

4. The compound or salt thereof according to claim 1, wherein in the formula (1) $R^1$ is a nitrogen atom and $R^2$ is a substituent represented by the formula (3).

5. The compound or salt thereof according to claim 1, wherein the radioactive iodine is one selected from the group consisting of $^{123}$I, $^{124}$I, $^{125}$I, and $^{131}$I.

6. An imaging agent used for imaging a tau protein, the imaging agent comprising the compound or salt thereof according to claim 1.

7. The imaging agent according to claim 6, wherein it is used for single photon emission computed tomography (SPECT).

8. The imaging agent according to claim 6, wherein it is used for diagnosis of a tauopathy.

9. An injection comprising the compound or salt thereof according to claim 1.

10. A radioactive iodine labeling precursor comprising a compound represented by the following formula (4) or a salt thereof,

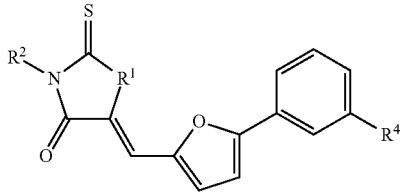
(4)

wherein, in the formula (4), $R^1$ is a sulfur atom or a nitrogen atom, $R^2$ is a substituent represented by the following formula (2),

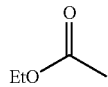
(2)

or the following formula (3),

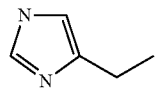
(3)

and $R^4$ is a trialkylstannyl substituent with alkyl chains having a length of 1 to 4 carbon atoms, a trialkylammonium substituent with alkyl chains having a length of 1 to 4 carbon atoms, or a triphenylstannyl substituent.

11. A method for producing a compound represented by the following formula (1) or a salt thereof,

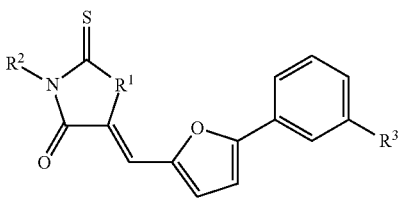
(1)

wherein, in the formula (1), $R^1$ is a sulfur atom or a nitrogen atom, $R^2$ is a substituent represented by the following formula (2),

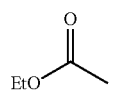
(2)

or the following formula (3),

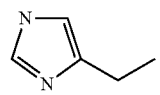
(3)

and $R^3$ is a radioactive iodine, the method comprising radio-iodinating the radioactive iodine labeling precursor of claim 10.

* * * * *